(12) United States Patent
Lutz

(10) Patent No.: US 7,667,370 B2
(45) Date of Patent: Feb. 23, 2010

(54) GENERATING DEVICE FOR GENERATING A USEFUL STREAM OF A MEDIUM, IN PARTICULAR FOR GENERATING SOUND

(75) Inventor: Josef Lutz, Vienna (AT)

(73) Assignee: NXP B.V., Eindhoven (NL)

( * ) Notice: Subject to any disclaimer, the term of this patent is extended or adjusted under 35 U.S.C. 154(b) by 874 days.

(21) Appl. No.: 10/546,306

(22) PCT Filed: Feb. 26, 2004

(86) PCT No.: PCT/IB2004/050166

§ 371 (c)(1), (2), (4) Date: Aug. 19, 2005

(87) PCT Pub. No.: WO2004/077880

PCT Pub. Date: Sep. 10, 2004

(65) Prior Publication Data

US 2008/0191582 A1   Aug. 14, 2008

(30) Foreign Application Priority Data

Feb. 27, 2003  (EP) ................................. 03100482

(51) Int. Cl.
*H01L 41/09* (2006.01)
*H03G 1/00* (2006.01)
(52) U.S. Cl. ..................... 310/317; 310/323.01; 381/97
(58) Field of Classification Search ............ 310/323.01, 310/324, 328, 317; 381/77, 89, 97; 318/116; 340/870.25, 870.26
See application file for complete search history.

(56) References Cited

U.S. PATENT DOCUMENTS

| 1,526,319 | A | * | 2/1925 | Chubb | 381/190 |
| 3,361,067 | A | * | 1/1968 | Webb | 417/322 |
| 6,850,623 | B1 | * | 2/2005 | Norris et al. | 381/97 |
| 2002/0017834 | A1 | * | 2/2002 | MacDonald | 310/328 |
| 2005/0046309 | A1 | * | 3/2005 | Kim et al. | 310/328 |
| 2006/0232167 | A1 | * | 10/2006 | Jordan | 310/324 |

FOREIGN PATENT DOCUMENTS

| GB | 2 013 311 | A | * | 8/1979 |
| JP | 1-219399 | A | * | 9/1989 |
| JP | 7-301180 | A | * | 11/1995 |
| JP | 9-257143 | A | * | 9/1997 |

\* cited by examiner

*Primary Examiner*—Thomas M Dougherty

(57) ABSTRACT

A generating device (1) for generating a useful stream of a medium (2) comprises at least a medium stream source (14) for generating a high-frequency medium stream (15) and at least a medium stream diode (36, 37) for cooperating with the generated medium stream (15), and at least one medium stream sink (40, 41) for cooperating with the medium stream influenced by the medium stream diodes (36, 37), wherein the at least one medium stream sink (40, 41) suppresses high-frequency stream components in the medium stream such that a useful medium stream (2) in a low-frequency range is obtained.

11 Claims, 2 Drawing Sheets

GENERATING DEVICE FOR GENERATING A USEFUL STREAM OF A MEDIUM, IN PARTICULAR FOR GENERATING SOUND

The invention relates to a generating device, which generating device is provided and designed for generating a useful stream of a medium with at least a flow velocity, which flow velocity can be varied with a useful frequency lying within a first frequency range, and which generating device comprises at least a medium stream source for generating at least a medium stream in alternating mutually opposed flow directions, which mutually opposed flow directions alternate with a frequency lying within a second frequency range, said second frequency range covering frequencies which lie above those of the first frequency range.

A generating device of the kind described in the opening paragraph is known, for example, from the patent document WO 01/33902 A2. This generating device is a device for generating a useful flow of air as the useful stream of a medium. Such a generating device is also denoted a parametric loudspeaker in the expert field. The known generating device comprises a plurality of ultrasound sources as the medium stream sources, each generating an ultrasound signal and projecting it into the space surrounding the ultrasound sources, which leads to a vibratory excitation of the air present in this space and thus to air flows in alternating mutually opposed flow directions. The known solution utilizes the physical effect that the projection of two ultrasound signals into a space containing air will lead to a superimposition of the projected ultrasound signals owing to the non-linear properties of the air, which superimposition also leads to a differential signal which results in audible sound.

It is required for the known solution that ultrasound signals are projected with a comparatively high energy content into the space containing the air so as to obtain audible sound with a sufficiently high energy content. The level of the required ultrasound energy to be generated must lie above the level of audible sound energy required for a faultless sound reproduction by several orders of magnitude, which is unfavorable in view of an optimized energy balance. Furthermore, the generation of audible sound depends on the properties of the air and especially on changes in these properties, which is unfavorable as regards a generation of audible sound that is of a consistent quality. Furthermore, the known solution involves the problem that a comparatively complicated constructional expenditure is necessary, which is unfavorable for realizing the product in as economical and inexpensive a manner as possible.

The invention has for its object to eliminate the above problems and to provide an improved generating device.

To achieve the above object, inventive features are provided in a generating device according to the invention such that a generating device according to the invention can be characterized as follows:

a generating device, which generating device is provided and designed for generating a useful stream of a medium with at least a flow velocity, which flow velocity can be varied with a useful frequency lying within a first frequency range, and which generating device comprises the following means:

at least a medium stream source for generating at least a medium stream in alternating mutually opposed flow directions, which mutually opposed flow directions alternate with a frequency lying within a second frequency range, said second frequency range covering frequencies which lie above those of the first frequency range, and at least a medium stream diode which is provided, constructed and arranged for cooperating with a stream of a medium generated by at least one medium stream source and which, in dependence on the flow direction of the stream of a medium cooperating therewith, works counter to said stream of the medium with flow resistances of different values, which leads to a total medium stream flowing in a transmission direction of the at least one medium stream diode, and at least one medium stream sink which is provided, constructed, and arranged for cooperating with the total medium stream generated by means of the at least one medium stream diode and which suppresses the stream components within the second frequency range contained in the total medium stream, resulting in the useful stream of the medium in the first frequency range without the suppressed stream components in the second frequency range at the output of the at least one medium stream sink.

The provision of the features according to the invention achieves that at least one medium stream source provided and constructed for generating a comparatively high-frequency medium stream in conjunction with only few, comparatively simple additional components is capable of generating a useful stream of a medium which lies in a frequency range substantially lower than the frequency of the medium stream generated by the at least one medium stream source, such that the generation of the useful stream of the medium is substantially independent of the medium surrounding the generating device. This achieves the essential advantage over the solution according to the prior art that the generation of the useful stream of the medium is substantially independent of changes in the properties of the medium surrounding the generating device, i.e. because the generated useful stream of the medium is generated substantially inside the generating device and enters the medium surrounding the generating device after being generated, so that the medium surrounding the generating device is not utilized for the actual generation of the useful stream of the medium. A further advantage is that only very small high-frequency flow components are obtained outside the generating device, since such high-frequency flow components are only formed by the flow components remaining after the suppression by means of the at least one medium stream sink.

The generating device according to the invention for generating a useful stream of a medium may handle a liquid as its medium, for example blood or plasma or an infusion liquid, which is to be supplied to a patient, in which case the generating device according to the invention practically performs the function of a pump or infusion pump. It was found to be advantageous, however, if the generating device according to the invention in addition has the characteristics of claim 2. Such a construction was found to be very advantageous because acoustically perceivable sound can be generated with such a construction in a very simple manner.

It was found to be particularly advantageous in an embodiment of a generating device according to the invention as mentioned in the preceding paragraph if in addition the characteristics of claim 3 are provided. Such a solution provides the advantage that such an ultrasound source can be modulated in a simple and satisfactory manner as regards the amplitude of the ultrasound vibrations that can be generated, so that the flow velocity of the air can be varied quickly and subtly. A continuous air flow or one with a slow modulation, i.e. with a frequency lying within the audible frequency range, can thus be generated.

In an embodiment of a generating device according to the invention as mentioned in the preceding paragraph, the ultrasound source may comprise a signal generator for generating an ultrasound signal with an unchangeable, fixed ultrasound frequency, which signal generator may be additionally fed with a modulation signal having an unchangeable, fixed frequency for modulating the ultrasound signal, in which case an acoustic signal with a permanent frequency is generated. It was found to be particularly advantageous in a generating device of the kind mentioned in the preceding paragraph, however, if in addition the characteristics of claim 4 are provided. This achieves the essential advantage that audible sound signals can be generated by the generating device whose frequency spectrum covers at least the entire audible range. For example, a sound reproduction in a frequency range between 0 Hz and 20,000 Hz is possible with such a construction. Sound reproduction far above 20,000 Hz is also possible, however, i.e. up to a frequency corresponding to half the frequency of the ultrasound vibration achievable by the ultrasound source, the sound reproduction then being the reproduction of modulated ultrasound.

The signal generator in a generating device of the construction described in the preceding paragraph may be designed for generating a carrier signal with an ultrasound frequency whose value is double the value of the highest frequency in the useful signal. It was found to be highly advantageous, however, if in addition the characteristics of claim 5 are provided. Such a construction offers the advantage that a useful stream of a medium is obtained which is homogeneous and comprises practically no interfering waveforms.

It was found to be highly advantageous in a generating device with at least one ultrasound source if two ultrasound sinks are provided. It is advantageously achieved thereby that a particularly good suppression of the high-frequency current component is obtained, and that a generating device with a high efficiency is obtained.

It was furthermore found to be advantageous in a generating device with at least one ultrasound source if a plurality of acoustic diodes is provided. This advantageously achieves a comparatively high degree of freedom in dimensioning the acoustic diodes, such that the total effective diameter is formed by a plurality of small diameters of the plurality of acoustic diodes, i.e. a larger effective diameter is available, however, in combination with a high rectifying efficiency of each individual acoustic diode, which is given by the small diameter of each acoustic diode.

It was found to be very advantageous in a generating device with a plurality of acoustic diodes if in addition the measures of claim 8 are taken. Such a construction was found to be particularly advantageous in practice, in particular with a view to a comparatively easy manufacture and to a construction that occupies as little space as possible.

It was found to be particularly advantageous in a generating device with an air flow chamber as referred to in the preceding paragraph if in addition the characteristics of claim 9 are provided. This leads to the advantage that a particularly high rectifying effect is obtained.

It was furthermore found to be advantageous in a generating device with an air flow chamber if the acoustic diodes comprise funnel-shaped holes which are designed for generating turbulent air flows. Such a construction was found to be advantageous with a view to a comparatively simple manufacture of the acoustic diodes, because the shape and dimensions of the funnel-shaped holes, which are substantially responsible for the generation of so-termed turbulent air flows, can be manufactured in a comparatively simple manner with good reproducibility.

It was found to be particularly advantageous in a generating device according to the invention if all components of the generating device are manufactured in integrated circuit technology from solid state elements that can be integrated. This achieves the major advantage that a large number of generating devices according to the invention can be manufactured in a comparatively simple manner as micromechanical products with the use of processes and methods known from semiconductor technology.

The above and further aspects of the invention will become apparent from the embodiments described below and are clarified with reference to these embodiments.

The invention will be described in more detail below with reference to three embodiments shown in the drawings, to which embodiments, however, the invention is not limited.

Figure 1:
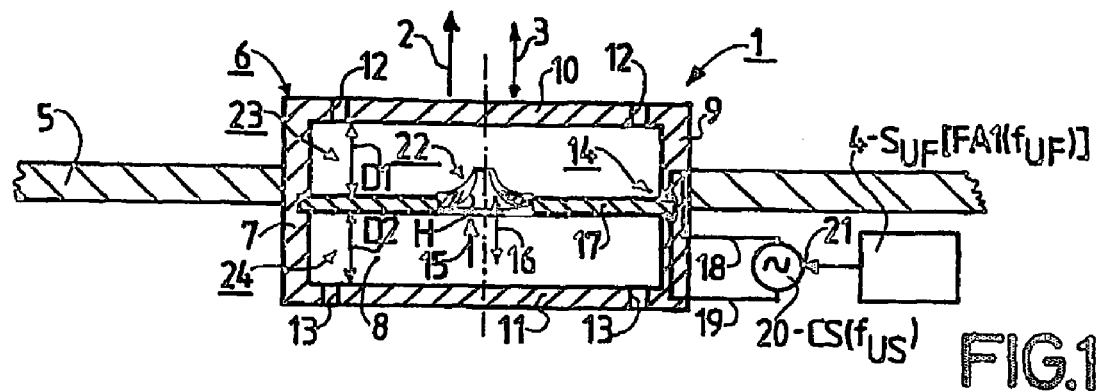
FIG. 1 is a strongly diagrammatic cross-sectional view of a generating device in a first embodiment of the invention, which generating device is designed for generating a useful flow of air and comprises an ultrasound source and an acoustic diode.

FIG. 1 shows a generating device 1. The generating device 1 is designed for generating a useful stream of a medium, i.e. a useful flow of air in the present case. The useful flow of air is diagrammatically indicated with an arrow 2 in FIG. 1. Many flow velocities occur in the air flow 2, indicated by a double arrow 3 in FIG. 1. The flow velocities 3 can be varied with a useful frequency $f_{UF}$ lying within a first frequency range FA1. In the present case, this relates to a first frequency range FA1 corresponding essentially to the audible frequency range, from approximately 10.0 Hz to 18,000 Hz in this case. The first frequency range FA1 may alternatively extend from 1.0 Hz to 20,000 Hz. Even frequencies below 1.0 Hz and even a zero frequency are possible. In the present case, the first frequency range FA1 is defined by a frequency range in which a useful signal $S_{UF}$ (cf. FIG. 4) provided by a signal source 4 is situated, which useful signal has a frequency spectrum lying mainly in the audible range.

In the present case, the generating device 1 is designed for generating a useful flow of air 2 which lies in the audible frequency range, as was noted above. This means, in other words, that the generating device 1 is provided and constructed for the generation of sound, more particularly audible sound, and thus fulfills the function of a loudspeaker. The generated useful air flow 2, i.e. the audible sound, may serve for generating and reproducing a speech signal here. Alternatively, the useful air flow 2 may serve to reproduce music signals. In the simplest case, the useful air flow 2 may serve to generate a call signal or warning signal having one given frequency. The generating device 1 is accommodated in a partition wall 5 so as to be able to perform the function of a loudspeaker, as has long been known from traditional loudspeakers, for example electromagnetic loudspeakers.

The generating device 1 has the major advantage that all components of the generating device 1 are manufactured from solid state elements in integrated technology. This means that the generating device 1 is manufactured on the basis of a solid state substrate, preferably by means of a semiconductor substrate such as a silicon substrate. This offers the major advantage that a very large number of such generating devices 1 can be manufactured in a single integration process.

The generating device 1 has a substantially cuboid housing 6, of which housing 6 three side walls 7, 8, and 9 as well as a front wall 10 and a rear wall 11 are shown in FIG. 1. The fourth side wall of the housing 6 is not visible in the cross-sectional view of FIG. 1. A plurality of sound passage openings 12 are provided in the front wall 10. The sound passage openings 12 are designed for allowing air to issue from the interior of the housing 6 and to flow through said openings in such a manner that the useful air flow 2 is obtained after passage through the sound passage openings 12. Air passage openings 13 are similarly provided in the rear wall 11, rendering possible an introduction of air into the interior of the housing 6. A cross-section through the housing 6 taken perpendicularly to the side walls 7, 8, and 9 will have a rectangular shape because of the substantially cuboid construction of the housing 6. The housing 6, however, may alternatively have a square or circular or elliptical or hexagonal cross-section.

The generating device 1 comprises a medium stream source 14 for generating a medium stream 15, which medium stream 15 is indicated with an arrow 15 in FIG. 1. The medium stream 15 in the present case is an air flow 15. Mutually opposed flow directions 16 occur in alternation in the air flow 15, which mutually opposed flow directions 16 are indicated by a further double arrow 16 in FIG. 1. The mutually opposed flow directions 16 alternate with a frequency $f_{US}$ lying in a second frequency range FA2. The second frequency range FA2 covers frequencies that lie above those of the first frequency range FA1, the frequency $f_{US}$ being an ultrasound frequency. The ultrasound frequency $f_{US}$ in the present case is approximately 4 MHz. The ultrasound frequency $f_{US}$ may alternatively lie between 40 kHz and 100 MHz, possibly even 200 MHz.

The ultrasound source 14 comprises a planar piezo element 17. The planar piezo element 17 is retained by its edge region in the side walls 7, 8, and 9 and in the invisible side wall of the housing 6. The piezo element 17 is movable in the mutually opposed flow directions of arrow 16 in an ultrasonic vibration. The piezo element 17 consists essentially of a carrier layer of a non-conductive material which is provided on its two main surfaces with respective electrically conducting coatings. Such a construction of a piezo element is generally known in the art. Such a piezo element 17 may also be regarded as a rigid membrane.

A signal generator 20 of the ultrasound source 14 is connected to the two coatings of the piezo element 17 via two respective connection lines 18 and 19 passed through the side wall 9. The signal generator 20 is designed for generating a carrier signal CS with the ultrasound frequency $f_{US}$. The signal generator 20 in addition comprises a connection terminal 21 for supplying the useful signal $S_{UF}$. The signal generator 20 is so constructed here that the signal generator 20 is suitable for modulating the carrier signal CS in dependence on the useful signal $S_{UF}$. It is achieved thereby, as is visible in FIG. 4, that the carrier signal CS is modulated as a function of the useful signal $S_{UF}$, so that major changes in the amplitude of the ultrasonic vibration given off by the ultrasound source 14 and as a result major changes in the amplitude of the useful air flow 2 can be achieved, resulting in a high sound volume.

It is to be noted on the signal generator 20 for the generation of the carrier signal CS that this signal generator 20 is designed for generating a carrier signal CS with an ultrasound frequency $f_{US}$ whose value in the present case is 200 times the value of the highest frequency in the useful signal $S_{UF}$.

Figure 4:
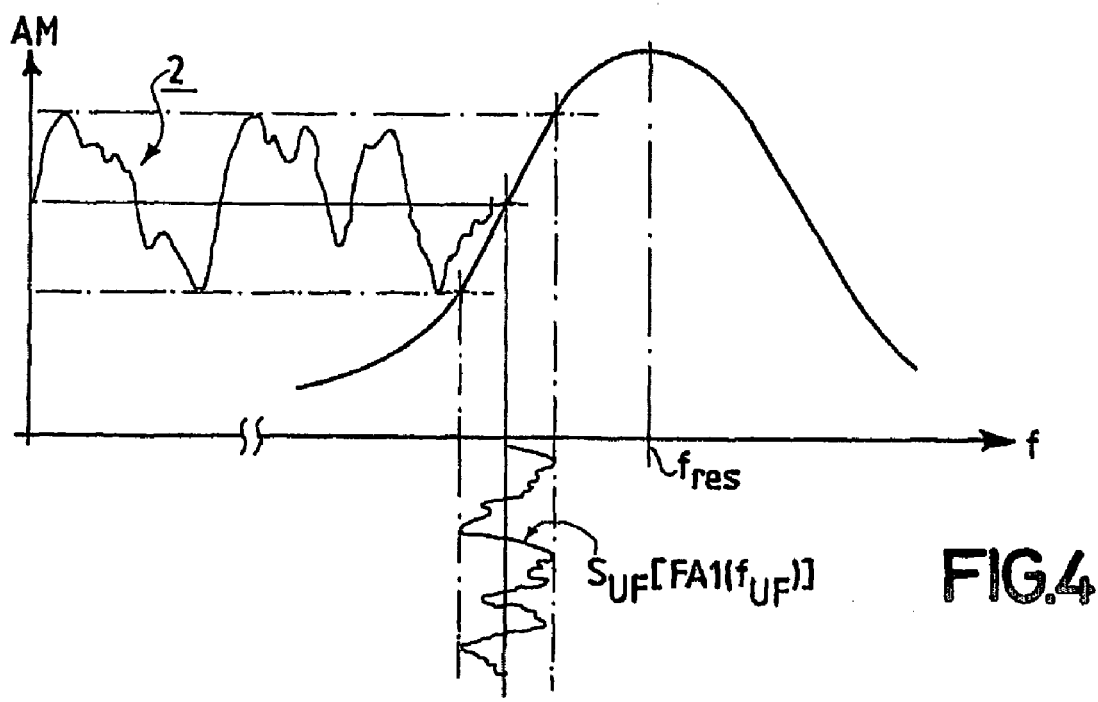
FIG. 4 is a diagram showing the dependence of the amplitude of an ultrasound vibration on the excitation frequency, which ultrasound vibration can be generated by the ultrasound source contained in the generating device of FIG. 1.

It is to be noted on the ultrasound source 14 that the ultrasound source 14 is operated in the region of its resonance frequency $f_{res}$, as is also visible in FIG. 4. In the case shown in FIG. 4 of the generating device 1 as shown in FIG. 1, the oscillation amplitude of the ultrasound vibration of the ultrasound source 14 in the region adjacent the resonance frequency $f_{res}$ is varied by the change in the supply frequency, which takes place by means of the supplied useful signal $S_{UF}$. It is to be noted that the oscillation amplitude of the ultrasonic vibration of the ultrasound source 14 may alternatively be varied through variation of the resonance frequency $f_{res}$ of the ultrasound source 14. The upper limit frequency of the generating device 1 of FIG. 1 is determined inter alia also by the ultrasound source 14. In addition, the upper limit frequency is also determined by two so-termed sink chambers, which sink chambers will be discussed in more detail further below.

The generating device 1 further comprises a medium stream diode 22 which is formed by an acoustic diode 22 in this case. The acoustic diode 22 is arranged in the center of the piezo element 17 in this case and is connected to the piezo element 17. The acoustic diode 22 is provided, constructed, and arranged so as to cooperate with the medium stream 15 generated by the ultrasound source 14, i.e. with the air flow 15 generated by the ultrasound source. The acoustic diode 22 consists of a spire-type elevation narrowing in the direction of the front wall 10, in which elevation a funnel-type hole H is provided. The hole H is shaped such that so-termed turbulent air flows can be generated by this hole H. Such turbulent air flows are necessary for achieving the desired effect. So-termed laminar flows are not suitable in the present case. The acoustic diode 22 counteracts the air flow 15 cooperating therewith by means of flow resistances of different values in dependence on the flow direction 16 of this air flow 15. Given a constant amplitude of the ultrasonic vibration generated by the ultrasound source 14, this will result on average in a constant air flow 15 in the forward direction defined by the acoustic diode 22. When the amplitude of the ultrasonic vibration generated by the ultrasound source 14 is varied—in dependence on the useful signal $S_{UF}$ in the present case—the quantitative value of the average air flow 15 in the forward direction defined by the acoustic diode 22 will change. In other words, the provision of the acoustic diode 22 results in a total flow of the medium in a forward direction of the acoustic diode 22.

The generating device 1 here comprises two medium stream sinks 23 and 24. The two medium stream sinks 23 and 24 are formed here by a first sink chamber 23 and a second sink chamber 24. The first sink chamber 23 lies between the front wall 10 of the housing 6 and the piezo element 17. The second sink chamber 24 lies between the rear wall 11 of the housing 6 and the piezo element 17. The two sink chambers 23 and 24 may be realized through the manufacture of two so-termed sacrificial layers in the integration process mentioned above during the manufacture of the generating device 1, which layers are removed again in the course of the integration process, as it has long been known per se. The dimension D1 of the first sink chamber 23 and the dimension D2 of the second sink chamber 24 may have a value of approximately 0.1 mm in practice.

The two sink chambers 23 and 24 are provided, constructed, and arranged for cooperation with the total medium stream generated by the ultrasound source 14 and the acoustic diode 22. The dimensions of the two sink chambers 23 and 24 are chosen in relation to the frequencies occurring in the generated total medium stream, such that the two sink chambers 23 and 24 suppress the flow components in the second frequency range FA2 present in the total medium stream, which results in a useful flow without the suppressed flow components downstream of the sink chambers 23 and 24. This means that the first sink chamber 23 at the output of said first sink chamber 23 yields the useful stream of the medium 2, i.e. the useful air flow 2, in accordance with the first frequency range FA1 without the suppressed flow components in the second frequency range FA2. The first sink chamber 23 and the second sink chamber 24 in the generating device 1 are dimensioned such that they are both ultrasound sinks.

It should also be noted on the dimensioning of the two sink chambers 23 and 24 that the dimensions D1 and D2 measured parallel to the flow directions 16 are chosen such that the formation of a standing wave in the respective sink chamber is rendered possible in both sink chambers 23 and 24, which standing wave has a maximum in the region of the acoustic diode 22. This situation ensures an enhanced efficiency of the ultrasound source 14.

In the generating device 1 of FIG. 1, which forms a sound source, the generated flow of sound of the sound source is practically constant in principle over the entire frequency range as a function of the frequency. The linearity of the flow of sound as a function of the amplitude (harmonics) is practically only dependent on the linearity of the amplitude of the ultrasonic vibrations generated by the ultrasound source 14 as a function of the control signal controlling the ultrasound source 14, i.e. of the useful signal $S_{UF}$ to be reproduced, and may be electronically compensated if this should be necessary.

The two ultrasound sinks, i.e. the two sink chambers 23 and 24, each have a volume adapted to the essential ultrasound frequencies occurring in the present case, so that the sink chambers 23 and 24 filter out the ultrasound component, which again has the result that outside the housing 6 of the generating device 1 a useful air flow 2 is practically only present and active which corresponds to the first frequency range FA1 and whose amplitude can be varied with the use of the amplitude of the ultrasonic vibration generated by the ultrasound source 14.

It should be noted here that, given the construction of the acoustic diode 22 as an active diode controllable by a control signal, the variation in amplitude of the useful flow of air 2 beyond the ultrasound sink 23, i.e. the perceivable acoustic signal, can be obtained not only through the change in amplitude of the ultrasound signal that can be generated by the ultrasound source 14, but also by a change in frequency or in phase (frequency or phase modulation) of the control signal for the active diode.

Figure 2:
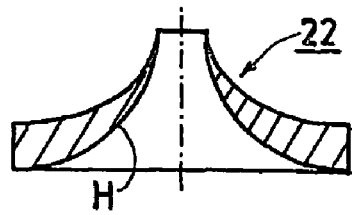
FIG. 2 is a cross-section on a larger scale than FIG. 1 of the acoustic diode of the generating device of FIG. 1.
Figure 3:
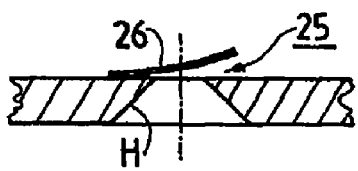
FIG. 3 shows in the same manner as FIG. 2 an acoustic diode in an alternative embodiment, which may equally well be used in the generating device of FIG. 1.

The acoustic diode 22 (cf. also FIG. 2) used in the generating device 1 is a so-termed passive acoustic diode 22 which comprises no moving components. Instead of such a purely passively constructed acoustic diode 22 as shown in FIG. 2, however, an acoustic diode 25 as shown in FIG. 3 may be used. The acoustic diode 25 of FIG. 3 also has a passage H, similar to the one provided in the acoustic diode 22 of FIG. 2. The difference in this passage H is that the passage H in the acoustic diode 25 of FIG. 3 approximately has a truncated cone shape, whereas the passage H in the acoustic diode 22 of FIG. 2 is funnel-shaped with a curved inner surface. The acoustic diode 25 of FIG. 3 is an acoustic diode of the so-termed valve type, said diode 25 being provided with a valve shutter 26. The valve shutter 26 can only be moved by the air flow generated by the ultrasound source 14 in the case of a passive construction of the acoustic diode 25, whereas in the case of an active construction of the acoustic diode 25 an active control of the position of the valve shutter can also be carried out, which control of the position of the valve shutter 26 may be achieved by means of the piezo effect and with the use of a control signal.

Figure 5:
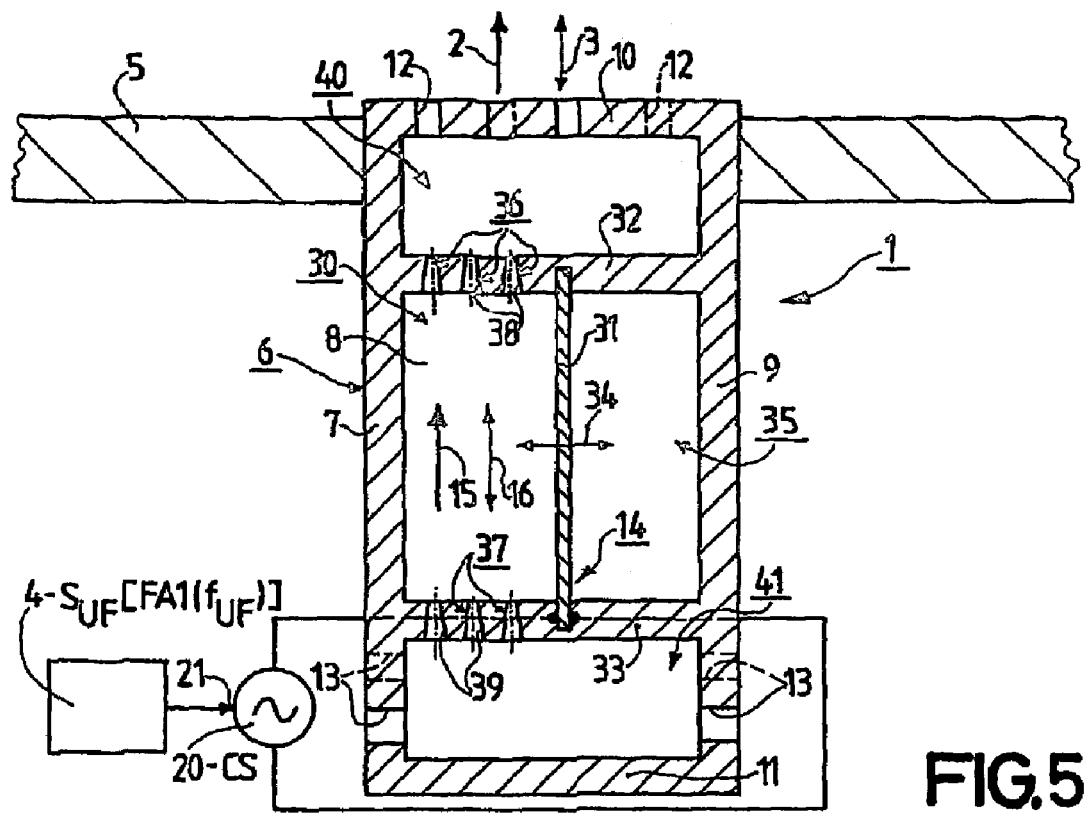
FIG. 5 is a strongly diagrammatic cross-sectional view of a generating device in a second embodiment of the invention.

FIG. 5 shows a generating device which is also manufactured in integrated technology, as was the generating device 1 of FIG. 1. Similar components of the generating device 1 in FIG. 5 have been given the same reference symbols as in FIG. 1.

The housing 6 of the generating device 1 of FIG. 5 comprises an air flow chamber 30 extending parallel to the mutually opposed flow directions 16. The air flow chamber 30 is bounded by the two side walls 7 and 8 and by the fourth side wall (not visible in FIG. 5) of the housing 6 opposite to the side wall 8. A further boundary wall of the air flow chamber 30 extending parallel to the mutually opposed flow directions 16 is bounded by means of a membrane, capable of vibration, of the ultrasound source 14. This membrane is again formed by a rigid planar piezo element 31, but no acoustic diode is directly connected to this piezo element 31 in the generating device 1 of FIG. 5. The piezo element 31 is connected by its edge region to the side wall 8 and to the fourth side wall (not visible in FIG. 5) of the housing opposite to the side wall 8, as well as to two boundary walls 32 and 33 extending transversely to the mutually opposed flow directions 16. The air flow chamber 30 is bounded transversely to the mutually opposed flow directions 16 by means of the two boundary walls 32 and 33. The membrane, i.e. the planar piezo element 31, is capable of vibration and can be made to vibrate parallel to the direction of the double arrow 34 in that a suitable excitation signal is applied to the piezo element 31, which excitation signal is supplied by the signal generator 20 via the lines 18 and 19 to the piezo element 31.

An additional chamber 35 is provided in the generating device 1 of FIG. 5 adjacent to the air flow chamber 30, which chamber 35 is bounded by the side wall 8 and the side wall 9 and the fourth side wall (not visible in FIG. 5) of the housing 6 opposite to the side wall 8, as well as by the boundary walls 32 and 33. The provision of the additional chamber 35 safeguards a faultless, interference-free vibration of the membrane, i.e. of the piezo element 31. The chamber 35 furthermore prevents a transmission of ultrasonic signals in a direction away from the air flow chamber 30, which is advantageous for achieving as high as possible an efficiency of the generating device 1.

Those portions of the boundary walls 32 and 33 in the generating device 1 that bound the air flow chamber 30 comprise a plurality of acoustic diodes 36 and 37. The acoustic diodes here essentially comprise holes 38 and 39 of truncated cone shape. The conical holes 38 and 39 are dimensioned and arranged such that the holes 38 and 39 are capable of generating turbulent air flows. The forward direction of the acoustic diodes 36 and 37 is the direction of the air flow 15 generated by the piezo element 31 of the ultrasound source 14. The distance between the two boundary walls 32 and 33 is chosen such that the formation of a standing wave is made possible in each of the two sink chambers 32 and 33, which standing wave has a maximum in the region of the acoustic diodes 36 and 37, which is advantageous for achieving as high as possible an efficiency of the generating device 1.

A first sink chamber 40 is provided adjacent the first boundary wall 32. The first sink chamber 40 is bounded by the side walls 7, 8, and 9 and by the fourth side wall (not visible in FIG. 5) and the first boundary wall 32, as well as the front wall 10 of the housing 6. Sound passage openings 12 are provided in the front wall 10.

A second sink chamber 41 is provided adjacent the second boundary wall 33. The second sink chamber 41 is bounded by the side walls 7, 8, and 9 and the fourth side wall (not visible in FIG. 5) of the housing 6, and by the second boundary wall 33 and the rear wall 11 of the housing 6. In this case the passage holes 13 provided for the supply of air into the second sink chamber 41 are arranged in the region of the side wall 7 and the side wall 9. The two sink chambers 40 and 41 each form an ultrasound sink.

The piezo element 31 of the ultrasound source 14 and the acoustic diodes 36 and 37 are mutually independently realized in the generating device 1 of FIG. 5, which is advantageous because it affords a higher degree of freedom in the construction and manufacture of these components, and in particular of the acoustic diodes 36 and 37.

Figure 6:
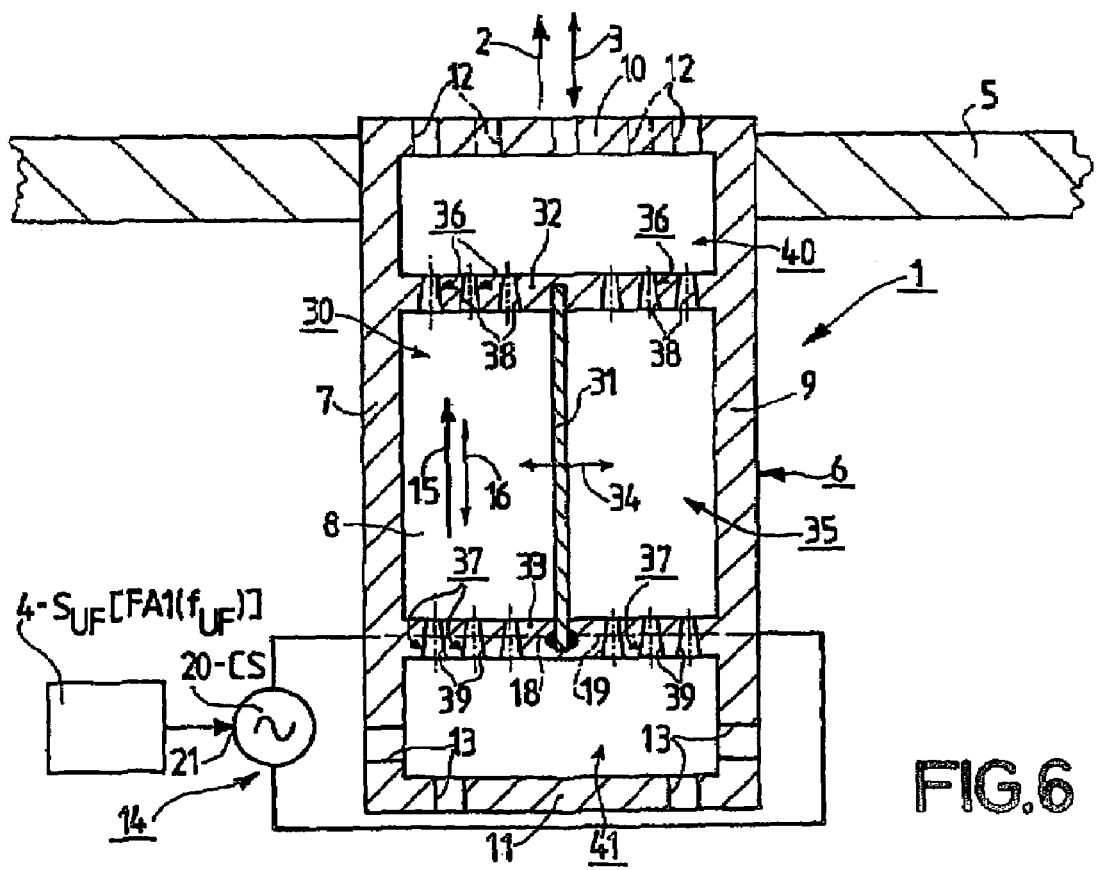
FIG. 6 shows in the same manner as FIG. 5 a generating device in a third embodiment of the invention.

FIG. 6 shows a generating device 1 which is a modification of the generating device 1 of FIG. 5.

The essential difference with the generating device 1 of FIG. 5 is that also the additional chamber 35 is constructed and utilized as an air flow chamber in the generating device 1 of FIG. 6. For this purpose, a plurality of acoustic diodes 36 and 37, also having funnel-shaped holes 38 and 39, are provided also in those portions of the boundary walls 32 and 33 extending transversely to the mutually opposed flow directions 16 that bound the additional chamber 35. In this case, too, the funnel-shaped holes 38 and 39 are dimensioned and arranged such that the holes 38 and 39 are capable of generating turbulent air flows. The generating device 1 of FIG. 6 has a higher efficiency than does the generating device 1 of FIG. 5 as regards the generation of sound.

The passage holes 13 are provided in the regions of the side wall 7, the side wall 9, and the rear wall 11 in the generating device 1 of FIG. 6.

In each of the embodiments of a generating device 1 described above, only a single medium stream source, i.e. an ultrasound source, is provided. It should be noted that more than one medium stream source, for example two or three or four or more ultrasound sources, may be provided in a generating device 1 according to the invention. If two medium stream sources are provided, they may be arranged next to one another and thus cooperate with medium stream diodes, which medium stream diodes may be aligned such that two generating devices 1 are obtained, which devices generate either two useful streams of the medium in the same direction, or to streams in mutually opposed directions, or two streams in crossing directions.

The invention claimed is:

1. A generating device (1) for generating a useful stream of a medium (2) comprising:
    at least a medium stream source (14) for generating at least a medium stream (15) in mutually opposed flow directions (16), modulating a first signal laying within a first frequency range to generate a second signal laying within a second frequency range, and alternating the mutually opposed flow directions (16) of the medium stream with the second signal lying within the second frequency range, said second frequency range covering frequencies that lie above those of the first frequency range;
    at least a medium stream diode (22; 25; 36, 37) provided, constructed and arranged for cooperating with a stream of a medium generated by the at least one medium stream source working counter to said stream of the medium with flow resistances, and generating a total medium stream flowing in a transmission direction of the at least one medium stream diode; and
    at least one medium stream sink (23, 24; 40, 41) provided, constructed, and arranged for cooperating with the total medium stream generated by the at least one medium stream diode, suppressing stream components within the second frequency range contained in the total medium stream, and generating the useful stream of the medium (2) in the first frequency range without the stream components within the second frequency range at an output of the at least one medium stream sink (23; 40).

2. A generating device (1) as claimed in claim 1, wherein the generating device (1) is designed for generating a useful flow of air (2).

3. A generating device (1) as claimed in claim 2, wherein the generating device (1) comprises at least one ultrasound source (14) as the medium stream source, at least one acoustic diode (22; 25; 36, 37) as the medium stream diode, and at least one ultrasound sink (23, 24; 40, 41) as the medium stream sink.

4. A generating device (1) as claimed in claim 3, wherein the ultrasound source (14) comprises a signal generator (20) for generating a carrier signal (CS) with an ultrasound frequency ($f_{US}$), wherein the signal generator (20) in addition comprises at least one connection terminal (21) for the supply of a useful signal ($S_{UF}$) with a frequency spectrum lying substantially in the audible range, and wherein the signal generator (20) is designed for modulating the carrier signal (CS) in dependence on the useful signal ($S_{UF}$).

5. A generating device (1) as claimed in claim 4, wherein the signal generator (20) is designed for generating a carrier signal (CS) with an ultrasound frequency ($f_{US}$) whose value is at least ten times the value of the highest frequency in the useful signal.

6. A generating device (1) as claimed in claim 3, wherein two ultrasound sinks (23, 24; 40, 41) are provided.

7. A generating device (1) as claimed in claim 3, wherein a plurality of acoustic diodes (36, 37) are provided.

8. A generating device (1) as claimed in claim 7, wherein at least one air flow chamber (30; 30, 35) extending parallel to the mutually opposed flow directions (16) is provided, wherein the at least one air flow chamber has at least one boundary wall that extends parallel to the mutually opposed flow directions (16) and that is formed by a membrane (31) of the ultrasound source (14), wherein the membrane is capable of vibration, and wherein the at least one air flow chamber has at least one boundary wall (32, 33) that extends transversely to the mutually opposed flow directions (16) and that comprises a plurality of acoustic diodes (36, 37), while a sink chamber (40, 41) forming an ultrasound sink is provided at least one boundary wall (32, 33) comprising a plurality of acoustic diodes (36, 37).

9. A generating device (1) as claimed in claim 8, wherein the two boundary walls (32, 33) of the at least one air flow chamber (30; 30, 35) extending transversely to the mutually opposed flow directions (16) comprise a plurality of acoustic diodes (36, 37), and wherein a sink chamber (40, 41) forming an ultrasound sink is provided adjoining the two boundary walls (32, 33) of the at least one air flow chamber (30; 30, 35) extending transversely to the mutually opposed flow directions (16).

10. A generating device (1) as claimed in claim 8, wherein the acoustic diodes (22) comprise funnel-shaped holes (H) that are formed so as to generate turbulent air flows.

11. A generating device (1) as claimed in claim 1, wherein all components of the generating device (1) are manufactured from solid state elements capable of integration in integrated technology.

* * * * *